United States Patent [19]

Nelson et al.

[11] Patent Number: 5,552,277

[45] Date of Patent: Sep. 3, 1996

[54] GENETIC DIAGNOSIS OF PROSTATE CANCER

[75] Inventors: William G. Nelson, Ruxton; William B. Isaacs, Glyndon, both of Md.; Wen-Hsiang Lee, Scottsdale, Ariz.

[73] Assignee: The Johns Hopkins University School of Medicine, Baltimore, Md.

[21] Appl. No.: 277,202

[22] Filed: Jul. 19, 1994

[51] Int. Cl.$^6$ .......................... C07H 21/02; C07H 21/04; C12Q 1/68

[52] U.S. Cl. .............................. 435/6; 435/18; 536/25.2; 536/24.3; 935/77; 935/78

[58] Field of Search ........................... 435/6, 18; 935/77, 935/78; 536/23.2, 24.3

[56] References Cited

U.S. PATENT DOCUMENTS 5,073,677  12/1991  Helmer et al. ..................... 800/205
5,298,393   3/1994  Urushizaki et al. ................ 435/7.1

Primary Examiner—W. Gary Jones
Assistant Examiner—Paul B. Tran
Attorney, Agent, or Firm—Fish & Richardson P.C.

[57] ABSTRACT

A method for detecting and a method for treating a cell proliferative disorder associated with glutathione-S-transferase (GSTP1) expression is provided. The method includes direct detection of a hypermethylated GSTP1 promoter, or indirect detection of decreased GSTP1 mRNA or GSTP1 protein in a suspect tissue sample.

10 Claims, 5 Drawing Sheets

GENETIC DIAGNOSIS OF PROSTATE CANCER

BACKGROUND OF THE INVENTION

1. Field of the Invention

This invention relates generally to the diagnosis of cancer and specifically to identification of a hypermethylated glutathione-S-transferase (GSTP1) promoter as a diagnostic indicator of prostatic tissue cellular proliferative disorder.

2. Description of Related Art

Current cancer tests are often nonspecific and therefore of limited clinical utility. For example, a biochemical test, widely used for both the diagnosis and monitoring of cancer, measures levels of carcinoembryonic antigen (CEA). CEA is an oncofetal antigen detectable in large amounts in embryonal tissue, but in small amounts in normal adult tissues. Serum of patients with certain gastrointestinal cancers contain elevated CEA levels that can be measured by immunological methods. The amount of CEA in serum correlates with the remission or relapse of these tumors, with the levels decreasing abruptly after surgical removal of the tumor. The return of elevated CEA levels signifies a return of malignant cells. CEA, however, is also a normal glycoprotein found at low levels in nearly all adults. Moreover, the relevance of CEA is severely compromised by the fact that this protein can be elevated in nonmalignant conditions and not elevated in many cancers. Therefore CEA is far from ideal as a cancer marker.

Human cancer cells typically contain somatically altered genomes, characterized by mutation, amplification, or deletion of critical genes. In addition, the DNA template from human cancer cells often displays somatic changes in DNA methylation (E. R. Fearon, et al., *Cell*, 61:759, 1990; P. A. Jones, et al., *Cancer Res.*, 46:461, 1986; R. Holliday, *Science*, 238:163, 1987; A. De Bustros, et al., *Proc. Natl. Acad. Sci., USA*, 85:5693, 1988); P. A. Jones, et al., *Adv. Cancer Res.*, 54:1, 1990; S. B. Baylin, et al., *Cancer Cells*, 3:383, 1991; M. Makos, et al., *Proc. Natl. Acad. Sci., USA*, 89:1929, 1992; N. Ohtani-Fujita, et al., *Oncogene*, 8:1063, 1993). However, the precise role of abnormal DNA methylation in human tumorigenesis has not been established. DNA methylases transfer methyl groups from the universal methyl donor S-adenosyl methionine to specific sites on the DNA. Several biological functions have been attributed to the methylated bases in DNA. The most established biological function is the protection of the DNA from digestion by cognate restriction enzymes. The restriction modification phenomenon has, so far, been observed only in bacteria. Mammalian cells, however, possess a different methylase that exclusively methylates cytosine residues on the DNA, that are 5' neighbors of guanine (CpG). This methylation has been shown by several lines of evidence to play a role in gene activity, cell differentiation, tumorigenesis, X-chromosome inactivation, genomic imprinting and other major biological processes. (Razin, A., H., and Riggs, R. D. eds. in DNA Methylation Biochemistry and Biological Significance, Springer-Verlag, N.Y., 1984).

Glutathione S-transferases (GSTs) catalyze intracellular detoxification reactions, including the inactivation of electrophilic carcinogens, by conjugating chemically-reactive electrophiles to glutathione (C. B. Pickett, et al., *Annu. Rev. Blochem.*, 58:743, 1989; B. Coles, et al., *CRC Crit. Rev. Biochem. Mol. Biol.*, 25:47, 1990; T. H. Rushmore, et al., *J. Biol. Chem.* 268:11475, 1993). Human GSTs, encoded by several different genes at different loci, have been classified into four families which have been referred to as α, μ, π, and theta (B. Mannervik, et al., *Biochem. J.*, 282:305, 1992).

Studies have shown that many human cancers exhibit increased GSTP1 expression relative to their tissues of origin (S. Tsuchida, et al., *CRC Crit. Rev. Biochem. Mol. Biol.*, 27:337, 1992). The limitation and failings of the prior art to provide meaningful markers which correlate with the presence of cell proliferative disorders, such as cancer, has created a need for markers which can be used to diagnose and monitor the course of such disorders. The present invention fulfills such a need.

SUMMARY OF THE INVENTION

The present invention is based on the unexpected discovery that most prostatic cancers contain decreased levels of GSTP1 polypeptide relative to normal prostatic tissue. Further study indicated that the reduced translation of GSTP1 in the cell was due to hypermethylation of the GSTP1 promoter, thereby resulting in decreased transcription of GSTP1.

In one embodiment, the invention provides a method for detecting a cell proliferative disorder in the prostatic tissue or other sample of a subject comprising contacting a cellular component with a reagent which detects GSTP1. A methylation sensitive restriction endonuclease can be utilized to identify a hypermethylated GSTP1 promoter, for example. In addition, decreased GSTP1 mRNA and GSTP1 protein can be detected by contacting a nucleic acid or protein samples from a suspected tissue with a GSTP1-specific nucleic acid probe or antibody, respectively, and comparing the levels with that of normal tissue.

In another embodiment, a method of treating a cell proliferative disorder associated with GSTP1 expression is provided. The method comprises administering to a subject with the disorder, a therapeutically effective amount of reagent such as a sense GSTP1 promoter and structural gene which modulates GSTP1 expression.

DETAILED DESCRIPTION OF THE INVENTION

Figure 1A:
FIG. 1 is shows immunohistochemical staining with anti-GSTP1 antisera of normal (panels A, B) prostatic tissue, prostatic intraepithelial neoplasia (PIN) (panel C) and prostatic cancer tissue (panels D-F).
Figure 1B:
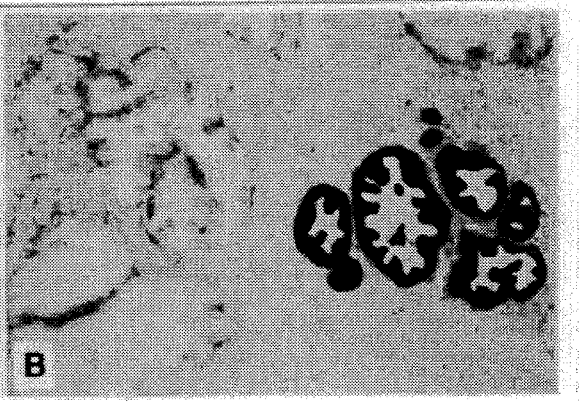
Figure 1C:
Figure 1D:
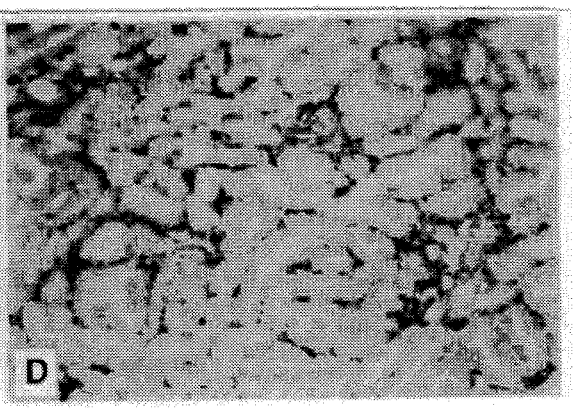
Figure 1E:
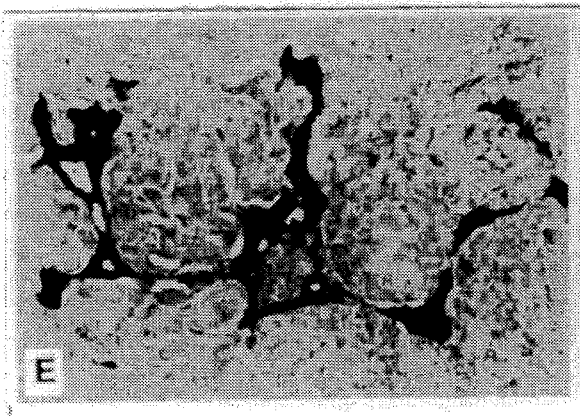
Figure 1F:

The present invention reveals that a hypermethylated promoter for the human π-class glutathione-S-transferase structural gene, GSTP1 positively correlates with prostatic carcinogenesis. This unexpected finding now allows the detection of prostate tissue cellular proliferative disorders by a simple assay that detects the hypermethylated promoter either directly, by restriction endonuclease analysis, or indirectly, by detection of GSTP1 mRNA or GSTP1 gene product. Methods of treatment which focus on replacing the hypermethylated promoter with a non-methylated promoter, for example, are now possible.

The term "promoter" refers to the regulatory region located upstream, or 5' to the structural gene. Sequence analysis of the promoter region of GSTP1 shows that nearly 72% of the nucleotides are CG and about 10% are CpG dinucleotides.

The invention provides a method for detecting a cell expressing GSTP1 or a cell proliferative disorder associated with GSTP1 in a tissue of a subject, comprising contacting a target cellular component suspected of expressing GSTP1 or having a GSTP1 associated disorder, with a reagent which binds to the component. The target cell component can be nucleic acid, such as DNA or RNA, or protein. When the component is nucleic acid, the reagent is a nucleic acid probe or PCR primer. When the cell component is protein, the reagent is an antibody probe. The probes can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the antibody, or will be able to ascertain such, using routine experimentation.

Since the present invention shows that a decreased level of GSTP1 transcription is often the result of hypermethylation of the GSTP1 promoter, it may be desirable to determine whether the promoter is hypermethylated. Actively transcribed genes generally contain fewer methylated CGs than the average number in DNA. Hypermethylation can be detected by restriction endonuclease treatment and Southern blot analysis. Therefore, in a method of the invention, when the cellular component detected is DNA, restriction endonuclease analysis is preferable to detect hypermethylation of the GSTP1 promoter. Any restriction endonuclease that includes CG as part of its recognition site and that is inhibited when the C is methylated, can be utilized. Preferably, the methylation sensitive restriction endonuclease is BssHII, MspI, or HpaII, used alone or in combination. Other methylation sensitive restriction endonucleases will be known to those of skill in the art.

For purposes of the invention, an antibody or nucleic acid probe specific for GSTP1 may be used to detect the presence of GSTP1 polypeptide (using antibody) or polynucleotide (using nucleic acid probe) in biological fluids or tissues. Oligonucleotide primers based on any coding sequence region in the GSTP1 sequence are useful for amplifying DNA, for example by PCR. Any specimen containing a detectable amount of polynucleotide or antigen can be used. A preferred sample of this invention is tissue of urogenital origin, specifically tissue of the prostate. Preferably the sample contains epithelial cells. Alternatively, biological fluids such as ejaculate, urine or blood may be used which may contain cells indicative of an GSTP1-associated cell proliferative disorder. Preferably the subject is human.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

The method for detecting a cell expressing GSTP1 of the invention or a cell proliferative disorder associated with an GSTP1, described above, can be utilized for detection of residual prostate cancer or other malignancies in a subject in a state of clinical remission. Additionally, the method for detecting GSTP1 polypeptide in cells is useful for detecting a cell proliferative disorder by measuring the level of GSTP1 in cells expressing GSTP1 in a suspect tissue in comparison with GSTP1 expressed in normal cells or tissue. Using the method of the invention, GSTP1 expression can be identified in a cell and the appropriate course of treatment can be employed (e.g., sense gene therapy or drug therapy). The expression pattern of the GSTP1 of the invention may vary with the stage of malignancy of a cell, for example as seen with prostatic intraepithelial neoplasia (PIN) (McNeal, et al., *Human Pathol.*, 17:64, 1986) therefore, a sample such as prostate tissue can be screened with a panel of GSTP1-specific reagents (i.e., nucleic acid probes or antibodies to GSTP1) to detect GSTP1 expression and diagnose the stage of malignancy of the cell.

Monoclonal antibodies used in the method of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of GSTP1. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

For purposes of the invention, GSTP1 may be detected by the monoclonal antibodies when present in biological fluids and tissues. Any sample containing a detectable amount of GSTP1 can be used. A sample can be a liquid such as ejaculate, urine, saliva, cerebrospinal fluid, blood, serum and the like, or a solid or semi-solid such as tissues, feces, and the like, or, alternatively, a solid tissue such as those commonly used in histological diagnosis.

In performing the assays it may be desirable to include certain "blockers" in the incubation medium (usually added with the labeled soluble antibody). The "blockers" are added to assure that non-specific proteins, proteases, or antiheterophilic immunoglobulins to anti-GSTP1 immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1–100 µg/µl) may be important, in order to maintain the proper sensitivity yet inhibit any unwanted interference by mutually occurring cross reactive proteins in the specimen.

In using a monoclonal antibody for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the GSTP1 antigert for which the monoclonal antibodies are specific.

The concentration of detectably labeled monoclonal antibody which is administered should be sufficient such that the binding to those cells having GSTP1 is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$AS, $^{89}$Zr, and $^{201}$TI.

A monoclonal antibody useful in the method of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

Monoclonal antibodies used in the method of the invention can be used to monitor the course of amelioration of GSTP1 associated cell proliferative disorder. Thus, by measuring the increase or decrease in the number of cells expressing GSTP1 or changes in GSTP1 present in various body fluids, such as ejaculate or urine, it would be possible to determine whether a particular therapeutic regiment aimed at ameliorating the disorder is effective.

The present invention also provides a method for treating a subject with an GSTP1-associated cell proliferative disorder. In prostate cancer, the GSTP1 nucleotide sequence is under-expressed as compared to expression in a normal cell, therefore, it is possible to design appropriate therapeutic or diagnostic techniques directed to this sequence. Thus, where a cell-proliferative disorder is associated with the expression of GSTP1 associated with malignancy, nucleic acid sequences that modulate GSTP1 expression at the transcriptional or translational level can be used. In cases when a cell proliferative disorder or abnormal cell phenotype is associated with the under expression of GSTP1, for example, nucleic acid sequences encoding GSTP1 (sense) could be administered to the subject with the disorder.

The term "cell-proliferative disorder" denotes malignant as well as non-malignant cell populations which often appear to differ from the surrounding tissue both morphologically and genotypically. Such disorders may be associated, for example, with absence of expression of GSTP1. Essentially, any disorder which is etiologically linked to expression of GSTP1 could be considered susceptible to treatment with a reagent of the invention which modulates GSTP1 expression.

The term "modulate" envisions the suppression of methylation of GSTP1 promoter or augmentation of other GST gene expression when GSTP1 is under-expressed. When a cell proliferative disorder is associated with GSTP1 expression, such methylation suppressive reagents as 5-azacytadine can be introduced to a cell. Alternatively, when a cell proliferative disorder is associated with under-expression of GSTP1 polypeptide, a sense polynucleotide sequence (the DNA coding strand) encoding the promoter region or the promoter operably linked to the structural gene, or GSTP1 polypeptide can be introduced into the cell.

The present invention also provides gene therapy for the treatment of cell proliferative disorders which are mediated by GSTP1. Such therapy would achieve its therapeutic effect by introduction of the appropriate GSTP1 polynucleotide which contains either a normal GSTP1 promoter region alone or in combination with a GSTP1 structural gene (sense), into cells of subjects having the proliferative disorder. Alternatively, the GSTP1 structural gene could be introduced operably linked to a heterologous promoter, such as the GSTM, GSTA or other promoter. Delivery of sense GSTP promoter polynucleotide constructs can be achieved using a recombinant expression vector such as a chimeric virus or a colloidal dispersion system.

The promoter polynucleotide sequences used in the method of the invention may be the native, unmethylated sequence or, alternatively, may be a sequence in which a nonmethylatable analog is substituted within the sequence. Preferably, the analog is a nonmethylatable analog of cytidine, such as 5-azacytadine. Other analogs will be known to those of skill in the art. Alternatively, such nonmethylatable analogs could be administered to a subject as drug therapy, alone or simultaneously with a sense promoter for GSTP1 or a sense promoter operably linked with the structural gene for GSTP1.

In another embodiment, a GSTP1 structural gene is operably linked to a tissue specific heterologous promoter and used for gene therapy. For example, a GSTP1 gene can be ligated to prostate specific antigen (PSA), prostate specific promoter for expression of GSTP1 in prostate tissue. Alternatively, the promoter for another GST gene can be linked to the GSTP1 structural gene and used for gene therapy.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GSTP1 sequence (including promoter region) of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the GSTP1 sense or antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Another targeted delivery system for GSTP1 polynucleotide is a colloidal dispersion system. Colloidal dispersion systems include macromolecule complexes, nanocapsules, microspheres, beads, and lipid-based systems including oil-in-water emulsions, micelies, mixed micelies, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting GSTP1 antibody-containing liposomes directly to the malignant tumor. Since the GSTP1 gene product may be indiscriminate with respect to cell type in its action, a targeted delivery system offers a significant improvement over randomly injecting non-specific liposomes. Preferably, the target tissue is urogenital and specifically is prostate tissue. Kidney and bladder tissue may also be utilized. A number of procedures can be used to covalently attach either polyclonal or monoclonal antibodies to a liposome bilayer. Antibody-targeted iiposomes can include monoclonal or polyclonal antibodies or fragments thereof such as Fab, or F(ab')$_2$, as long as they bind efficiently to an the antigenic epitope on the target cells. Liposomes may also be targeted to cells expressing receptors for hormones or other serum factors.

In yet another embodiment, the invention envisions treating a subject with low levels of GSTP1 expression with a glutathione-S-transferase inducing agent. Stimulation of the other classes of GSTs should compensate for the deficiency in GSTP1. Such inducers include sulfofurain, oltipraz, as well as other substances known in the art (Prochaska, et al., *Proc. Nat'l. Acad. Sci., U.S.A.*, 89:2394, 1992; Zhang, et al., *Proc. Nat'l. Acad. Sci., U.S.A.*, 89:2399, 1992; Prestera, et al., *Proc. Nat'l. Acad. Sci., U.S.A.*, 90:2965, 1993), The invention also relates to a medicament or pharmaceutical composition comprising a GSTP1 promoter polynucleotide or a GSTP1 or other GST promoter polynucleotide operably linked to the GSTP1 structural gene in a pharmaceutically acceptable excipient or medium wherein the medicament is used for therapy of GSTP1 associated cell proliferative disorders.

The following Examples are intended to illustrate, but not to limit the invention. While such Examples are typical of those that might be used, other procedures known to those skilled in the art may alternatively be utilized.

EXAMPLES

For human prostate cancer, the most commonly diagnosed cancer in men in the United States (C. C. Boring, et al., *Cancer J. Clin.*, 44:7, 1994), the present invention shows uniform somatic changes in DNA methylation at the glutathio one-S-transferase gene GSTP1 locus. The GSTP1 gene, encoding the human π-class GST, appears to be commonly inactivated as a result of promoter hypermethylation during prostatic carcinogenesis and, surprisingly, most prostatic cancers contained decreased levels of detectable GSTP1 poly-peptides relative to normal prostatic tissue.

The identification of alterations in the gene, GSTP1, and thus expression of the gene, which is associated with cancer cells and not normal cells provides an ideal marker for identification of a cell proliferative disorder. There is a need for new cancer markers which would allow more effective diagnosis and treatment regimes.

Example 1

π-CLASS GLUTATHIONE-S-TRANSFERASE EXPRESSION IN NORMAL AND NEOPLASTIC HUMAN PROSTATIC TISSUES

To assess GSTP1 expression in normal and neoplastic prostatic cells in vivo, tissue specimens were subjected to immunohistochemical staining using α-GSTP1 antibodies. Formalin-fixed paraffin-embedded prostatic tissue sections were assessed for GSTP1 expression by immunohistochemical staining with α-GSTP1 antiserum (Oncor) using an immunoperoxidase technique (Vectastain). FIG. 1 shows the results of immunostaining prostatic tissue with GSTP1 antibody.

In normal prostatic tissues, intense staining for GSTP1 was seen in almost all basal epithelial cells (see FIG. 1, panel A). Some normal glandular epithelial cells also appeared to contain immunoreactive GSTP1, while most contained no detectable enzyme (FIG. 1, panel B). Lobules with GSTP1-positive or with GSTP1-negative glandular epithelial cells did not differ in their histologic appearance or anatomic distribution. Otherwise, GSTP1-positive epithelial cells were detected all normal epithelial structures within prostatic tissue, including the verumontanum, the utricle, prostatic ducts, ejaculatory ducts, and the prostatic urethra. Positive immunohistochemical staining for GSTP1 was also seen in foci of transitional cell metaplasia, squamous cell metaplasia, and hyperplasia associated with benign prostatic hypertrophy (BPH). Despite the presence of abundant GSTP1 in most normal prostatic epithelial cells as well as in cells comprising benign proliferative prostatic lesions, 88 out of 91 specimens of prostatic carcinoma contained no detectable immunoreactive GSTP1 (FIG. 1, panels D, E, and F). Prostatic intraepithelial neoplasia (PIN) has been proposed to represent a premalignant lesion. Of interest, in a fraction of PIN lesions, many epithelial cells were also devoid of GSTP1 (FIG. 1, panel C).

Example 2

GSTP1 EXPRESSION IN HUMAN PROSTATIC CANCER CELL LINES

Figure 3A:
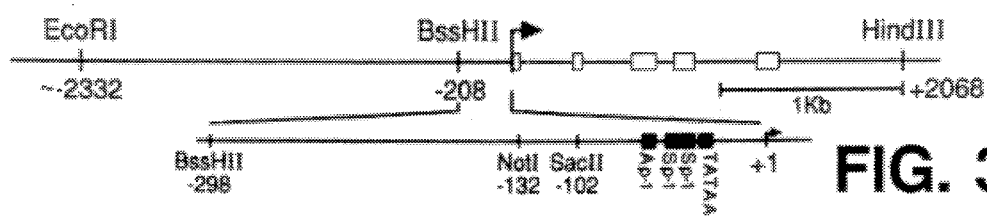
FIG. 3 shows a restriction map of the GSTP1 promoter (panel A), Southern blot of human prostatic cancer cell line DNA cut with BssHII (panel B) a restriction map of the GSTP1 gene (panel C) and a Southern blot of human prostatic cancer cell line DNA cut with MspI or HpaII (panel D).
Figure 3B:
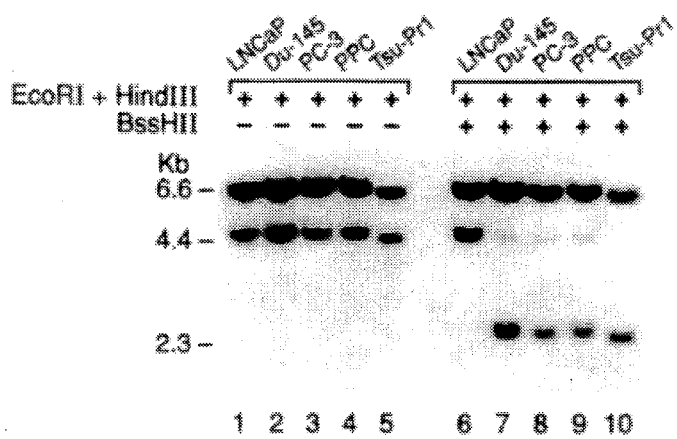
Figure 3C:
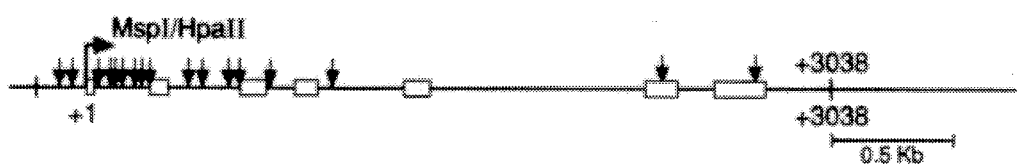
Figure 3D:
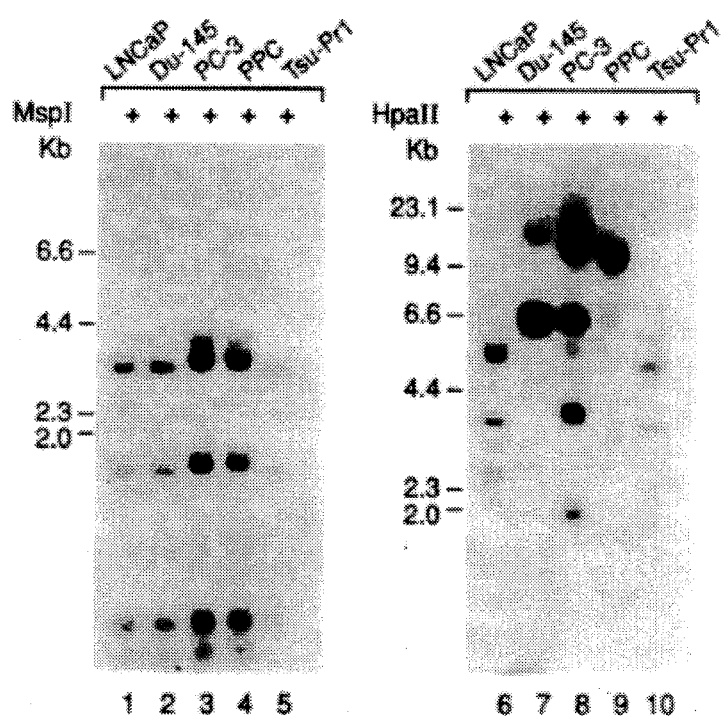

To study the molecular mechanisms underlying GSTP1 regulation in human prostate cancer, five well-established human prostatic carcinoma cells lines (K. R. Stone, et al., *Int. J. Cancer*, 21:274, 1978) were assessed for GSTP1 expression by immunoblot analysis for GSTP1 and by Northern blot analysis for GSTP1 mRNA. A restriction map of the GSTP1 promoter indicating $^{5'\text{-}me}$C-sensitive restriction enzyme recognition sites is shown in FIG. 3A. FIG. 3B shows a Southern analysis of human prostatic cancer cell line DNA cut with the $^{5'\text{-}me}$C-sensitive restriction enzyme BssHII and hybridized with a GSTP1 cDNA probe. DNA, isolated from growing cultures of each of the human prostatic cancer lines by sodium dodecylsulfate/proteinase K deproteinization followed by phenol/chloroform extractions, was digested first with HindIII and EcoRI and then with BssHII before being electrophoresed on agarose gels, transferred to Zetaprobe (BioRad) membranes, and then hybridized with $^{32}$p-labelled GSTP1 cDNA (American Type Culture Collection). FIG. 3C shows a restriction map of the GSTP1 gene showing recognition sites for MspI and HpaII (denoted by vertical arrows). FIG. 3D shows a southern analysis of human prostatic cancer cell line DNA cut with MspI or with HpaII (William C. Earnshaw, Johns Hopkins University School of Medicine, Baltimore, Md.; Robert Wood Johnson-University of Medicine and Dentistry of New Jersey, Piscataway, N.J.).

Cell lines were also tested by immunoblot analysis and Northern blot analysis. For immunoblots, saline-washed cultured prostatic carcinoma cells were collected by centrifugation at 14,000× g for 10 minutes at room temperature and then lysed in a protein extraction buffer (2% sodium dodecyl sulfate, 10% glycerol, and 10 mM dithiothreitol in 62 mM tris-HCl, pH 7.8) by heating to 95° C. for 10 minutes. The DNA content of each cell extract was estimated using a diphenylamine assay (Burton, *Methods Enzymol.*, 123:163, 1968). Equivalent total protein extracts prepared from each of the cultured cell lines were electrophoresed on polyacrylamide gels, transferred to nitrocellulose filters (Hybond-ECL; Amersham) using a semidry electroblotter (Millipore), and subjected to immunoblot analysis for GSTP1 and DNA topoisomerase I polypeptide levels using specific antisera in a manner previously described (Nelson, et al., *Mol. Cell. Biol.*, 14:1815, 1994). Rabbit α-GSTP1 antiserum was obtained from Oncor; human α-topoisomerase I was generously provided by William C. Earnshaw (Johns Hopkins University School of Medicine, Baltimore, Md.).

Northern blot analysis utilized total RNAs, extracted from cultured cells by the method of Chomczynski and Scacchi (*Anal. Biochem.*, 162:156, 1987) which were quantitated using an orcinol assay (Schneider, *Methods Enzymol.*, 3:680, 1957) and then electrophoresed on MOPS-formaldehyde agarose gels, transferred to Zetaprobe (BioRad) filters, and then assessed for GSTP1 and TOP1 mRNA levels by hybridization with specific cDNA probes. GSTP1 cDNA was obtained from the American Type Culture Collection; TOP1 cDNA was generously provided by Leroy F. Liu (Robert Wood Johnson-University of Medicine and Dentistry of New Jersey, Piscataway, N.J.).

Figure 2A:
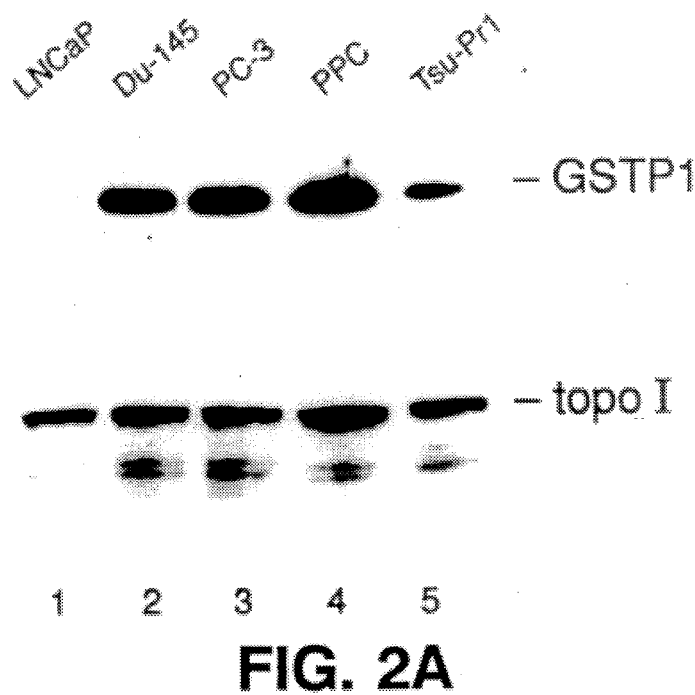
FIG. 2 shows immunoblot (panel A) and Northern blot (panel B) analyses of GSTP1 expression in human prostatic cancer cell lines.
Figure 2B:
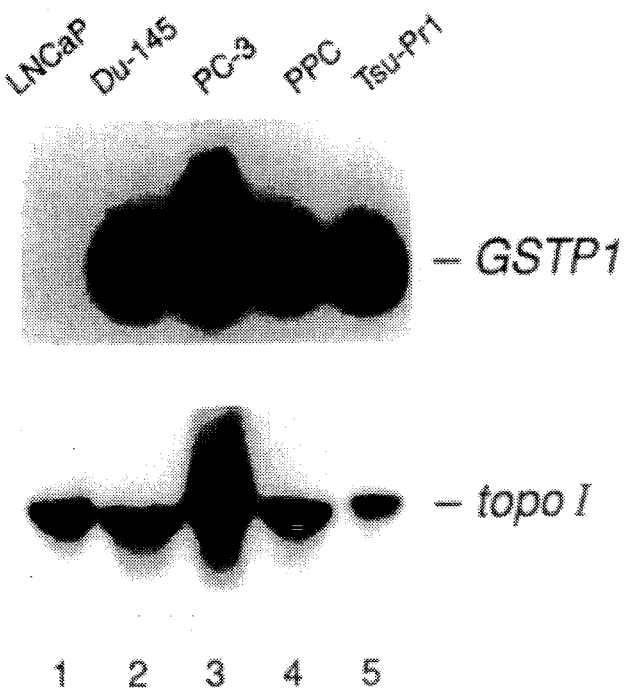

In accordance with the observed lack of GSTP1 expression by human prostatic cancers in vivo, immunoblot analysis using α-GSTP1 antisera failed to detect GSTP1 polypeptides in a protein extract prepared from LNCaP cells (FIG. 2A, lane 1), and Northern blot analysis of total RNA failed to detect GSTP1 mRNA in total RNA recovered from the LNCaP cell line (FIG. 2B, lane 1). In contrast, Du-145 cells, PC-3 cells, PPC cells, and TSU-Pr1 cells appeared to contain abundant GSTP1 polypeptides and GSTP1 mRNA (FIG. 2A and 2B, lanes 2-5).

Example 3

METHYLATION OF 5' REGULATORY SEQUENCES AT THE GSTP1 LOCUS IN PROSTATIC CANCER CELL LINES

Sequence analysis of the potential 5' regulatory region upstream of the GSTP1 gene has revealed a TATAA-box, tow potential SP1 binding sites, and a consensus AP-1 site (I. G. Cowell, et al., *Biochem. J.*, 255:79, 1988; C. S. Morrow, et al., *Gene*, 75:3, 1989). Functional promoter studies have established that a 72-nucleotide sequence located 5' of the transcriptional start site (from nucleotide −80 to −8) exhibits basal promoter activity when ligated to a promoterless chloramphenicol acetyltransferase (CAT) reporter gene in transient transfection assays (C. S. Morrow, et al., *Biochem. Biophys. Res. Comm.*, 176:233, 1991). Of note, the 400 nucleotides lying immediately 5' of the transcriptional start site contain nearly 72% CG nucleotides with 41 CpG dinucleotides. Methylation of CpG dinucleotides in regulatory regions of mammalian genes has been frequently associated with diminished transcriptional activity (I. Keshet, et al., *Proc. Natl. Acad. Sci., USA*, 82:2560, 1985; I. Keshet, et al., *Cell*, 44:535, 1986; H. Cedar, *Cell*, 53:3, 1988; J. Boyes, et al., *Cell*, 64:1123, 1991; J. D. Lewis, et al., *Cell*, 69:905, 1992). To determine whether differences in GSTP1 promoter methylation correlate with the differences in GSTP1 expression detected in the human prostatic cancer cell lines, DNA purified from each of the cell lines was digested with the $^{5'-me}$C-sensitive restriction enzyme BssHII and then subjected to Southern blot analysis using a GSTP1 probe.

DNA isolated from LNCaP cells and studied in this manner failed to cut BssHII (FIG. 3B, lane 6). The absence of BssHII digestion of LNCaP GSTP1 promoter DNA did not appear to be consequence of inadequate LNCaP DNA digestion by BssHII in general. When the Southern blots were hybridized with a TPI (Triose phosphate isomerase) gene probe (L. E. Maquat, et al., *J. Biol. Chem.*, 260:3748, 1985); J. R. Brown, et al., *Mol. Ceil. Biol.*, 5:1694, 1985), complete digestion at a BssHII site was evident (FIG. 3B).

In addition, the failure of BssHII to cut LNCaP GSTP1 promoter DNA likely resulted from cytosine methylation and not from mutation at the BssHII recognition site because GSTP1 promoter sequences amplified from LNCaP DNA by the polymerase chain reaction (PCR) were readily digested by BssHII. Furthermore, LNCaP GSTP1 regulatory sequence also failed to cut with the $^{5'-me}$C-sensitive restriction enzymes NotI and SacII, which recognize sites at -132 and -102 in the proximal GSTPI promoter, respectively. In contrast, hypomethylation of promoter sequences was found for the majority of GSTP1 alleles present in Du-145 cells, PC-3 cells, PPC cells, and Tsu-Pr1 cells (FIG. 3B). Each of these cell lines expresses abundant GSTP1 mRNA (see FIG. 2), suggesting an association of increased GSTP1 transcriptional activity with GSTP1 promoter hypomethylation.

Furthermore, Southern blot analysis of prostate cancer cell line DNAs digested with the isoschizomers MspI and HpaII, which have several recognition sites distributed throughout the GSTP1 gene, revealed that the correlation of cytosine hypomethylation with increased GSTP1 appeared to be restricted to cytosine residues present in 5' regulatory sequences (FIG. 3, C and D). As has been proposed for some CG-rich 5' regulatory sequences in other genes, the GSTP1 promoter sequences may constitute a methylation-sensitive "CpG island" (A. P. Bird, *Nature*, 321:209, 1986).

DNA methylation patterns have been found to change in cells propagated in vitro (F. Antequera, et al., *Cell*, 62:503, 1990). Of interest in this regard, Du-145 cells, PC-3 cells, and PPC cells appeared to contain both hypomethylated and hypermethylated GSTP1 promoter sequences. Each of the cell lines studies is known to contain greater than a diploid content of DNA/cell (K. R. Stone, et al., supra). While the majority of the GSTP1 promoter sequences were hypomethylated in the Du-145, PC-3, and PPC cell lines, Southern blot analysis indicated that each cell line contained a minority of GSTP1 promoter sequences which did not cut the $^{5'-me}$C-sensitive restriction enzyme BssHII (see FIG. 3), consistent with promoter hypermethylation involving at least one GSTP1 allele. As was the case for the LNCaP cell line, BssHII failure to cut GSTP1 promoter sequences in DNA from these cells occurred despite complete digestion of BssHII sites in the TPI gene (FIG. 3). DNA isolated from Tsu-Pr1 cells did not display any evidence of GSTP1 promoter methylation (FIG. 3). In all, methylated GSTP1 promoter sequences were present in 4 of 5 human prostatic cancer cell lines. If the GSTP1 genes were inactivated in the parent tumors for the cell lines by promoter hypermethylation, the Du-145, PC-3, PPC, and Tsu-Pr1 cell lines may have reactivated GSTP1 expression during continuous propagation in vitro as a result of promoter demethylation in some of the GSTP1 alleles.

Example 4

GSTP1 PROMOTER METHYLATION STATUS IN VIVO IN NORMAL ADULT TISSUES

Methylation of the GSTP1 promoter has not been previously described (V. Daniel, CRC Crit. *Rev. Biochem. Mol.*

Figure 4A:
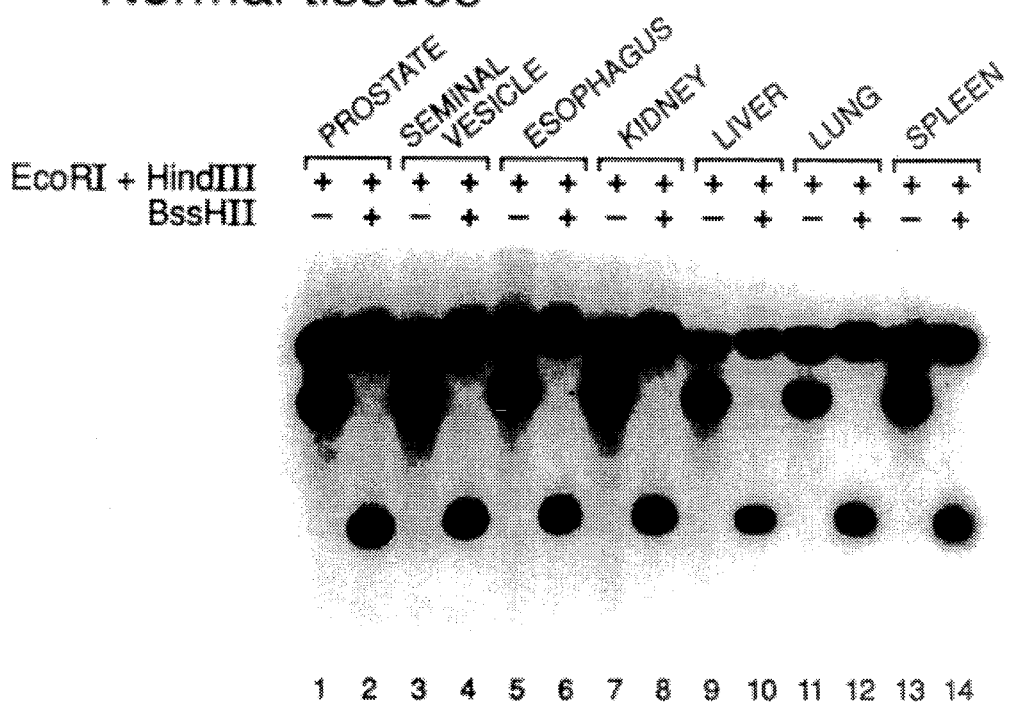
FIG. 4 shows Southern blot analyses or normal adult tissues digested with EcoRI and HindIII then with or without BssHII (panel A); and prostatic tissue DNA digested with EcoRI, HindIII and BssHII (panel B).
Figure 4B:
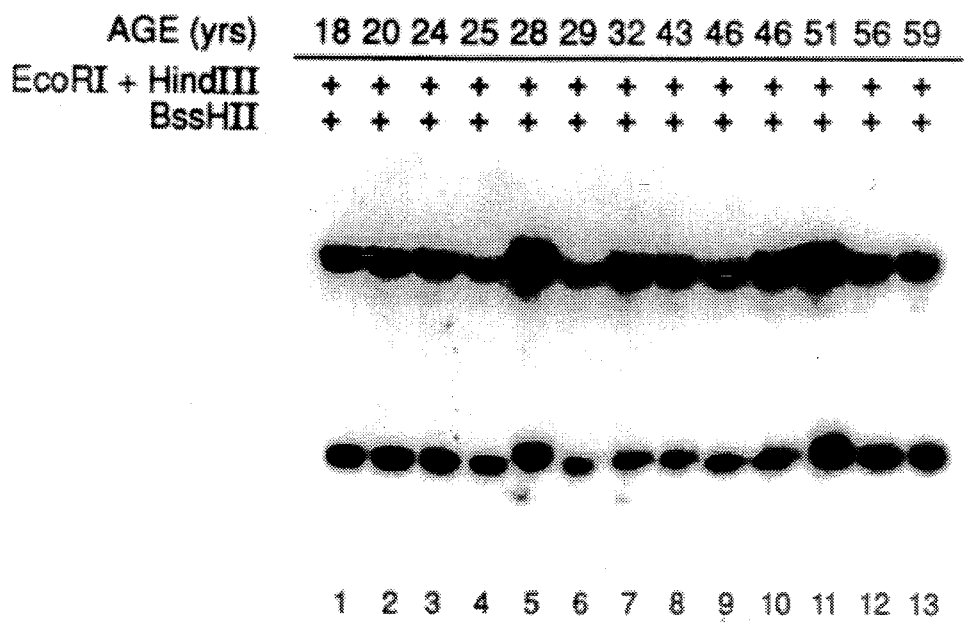

Biol., 28:173, 1993). To determine whether GSTP1 promoter hypermethylation occurs during normal physiologic cellular differentiation, DNA isolated from normal human tissues with different GSTP1 expression patterns was subjected to Southern blot analysis following digestion with the $5'$-$^{me}$C-sensitive restriction enzyme BssHII. Southern blot analyses using a GSTP1 cDNA probe of DNA isolated from normal human tissue specimens recovered at autopsy were accomplished as described above for FIG. 3. FIG. 4A shows normal tissues digested first with EcoRI and HindIII and then with or without BssHII. FIG. 4B shows DNA prepared from normal prostatic tissues recovered at autopsy from men of different ages who did not suffer from prostatic diseases, digested with EcoRI, HindIII, and BssHII.

No evidence of methylated GSTP1 promoter sequences were detected in DNA isolated from normal prostate, seminal vesicle, esophagus, kidney, liver, lung, or spleen (FIG. 4A).

To assess whether hypermethylation of GSTP1 promoter sequences arises during aging in normal prostatic cells, DNA prepared from normal prostate tissue specimens recovered from men of different ages was also analyzed (see FIG. 4B). Again, there was no evidence of GSTP1 promoter hypermethylation in any of the normal prostatic tissues.

Example 5

GSTP1 PROMOTER HYPERMETHYLATION IN PROSTATIC CARCINOMAS

Figure 5A:
FIG. 5 shows GSTP1 promoter hypermethylation in DNA from prostatic carcinomas. Panel A shows seminal visicle (SV) and prostatic carcinoma (CA) DNA: Panel B shows grossly normal prostate (PROS) and CA; and Panel C shows PROS, CA, and benign prostatic hyperplasia (BPH) from the same surgical resection specimens.
Figure 5B:
Figure 5C:
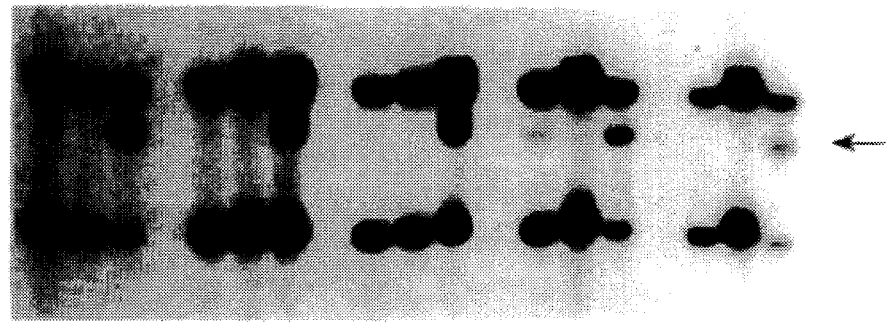

Hypermethylated GSTP1 promoter sequences were detected in DNA from the most of the human prostate cancer cell lines studied, but were rarely evident in DNA prepared from normal human tissues. Furthermore, the great majority of the human prostatic carcinoma specimens examined by immunohistochemical staining with αGSTP1 antibodies were devoid of GSTP1 expression. To determine whether GSTP1 promoter hypermethylation occurs during prostatic carcinogenesis in vivo, DNA isolated from human prostatic carcinoma specimens was digested with the $5'$-$^{me}$C-sensitive restriction enzyme BssHII and then subjected to Southern blot analysis using a GSTP1 probe (FIG. 5). DNA was isolated from prostatic carcinomas (CA) recovered by surgical resection. In addition, DNA was prepared from grossly normal prostatic tissue (PROS) adjacent to cancer tissue, from benign prostatic hyperplasia (BPH), and from normal seminal vesicles (SV) which accompanied the surgical resection specimen. The DNA was then digested with EcoRI, HindIII, and BssHII and subjected to Southern blot analysis using GSTP1 cDNA as described above in FIG. 3. FIG. 5A shows matched seminal vesicle (SV) and prostatic carcinoma (CA) DNA. FIG. 5B shows matched grossly normal prostate (PROS) and prostatic carcinoma (CA) DNA. FIG. 5C shows grossly normal prostate (PROS), benign prostatic hyperplasia (BPH), and prostatic carcinoma (CA) from the same surgical resection specimens. The arrow denotes migration position of GSTP1 restriction fragment uncut by BssHII.

Each of the prostate cancers studies displayed evidence of increased GSTP1 promoter hypermethylation relative to matched control DNA prepared from normal tissues (FIG. 5). For prostatic epithelial cells, increased methylation of GSTP1 promoter sequences may be specific to the process of malignant transformation. For five cases of prostate cancer surgically removed by radical prostatectomy, DNA was selectively prepared from different areas of the same prostatic tissue resection specimens containing normal prostate, benign prostatic hyperplasia (BPH), or prostatic cancer (FIG. 5C). When Southern blots containing BssHII-digested DNA samples were hybridized with a GSTP1 probe, apparent hypermethylation of GSTP1 promoter sequences was detected in each of the cancer specimens (FIG. 5C, lanes 3, 6, 9, 19, and 15), but non of the BPH specimens (FIG. 5C, lanes 2, 5, 8, 11, and 14). In one of the cases, DNA prepared from grossly normal prostatic tissue also appeared to contain GSTP1 alleles with some methylated promoter sequences (FIG. 5, lane 10). Whether this resulted from infiltration of grossly normal prostatic tissue by microscopic carcinoma containing methylated GSTP1 promoters, from GSTP1 promoter hypermethylation in prostatic intraepithelial neoplasia (PIN) lesions in the grossly normal prostatic tissue, or from GSTP1 promoter hypermethylation in histologically normal prostatic epithelial cells has not been established. However, hypermethylation of GSTP1 promoter DNA nonetheless appears specific to the process of neoplastic transformation in the prostate: normal prostatic tissues from men without prostate cancer did not contain detectable methylation of GSTP1 regulatory sequences (FIG. 4B).

All of the data collected in this study suggest that decreased GSTP1 expression and GSTP1 promoter hypermethylation occur commonly during the malignant transformation of prostatic epithelial cells. Regional methylation changes, often manifest as hypermethylation of CpG island sequences, have been proposed to play an important role in carcinogenesis (L.E. Maquat, et al., *J. Biol. Chem.*, 260:3748, 1985; J. R. Brown, et al., *Mol. Cell. Biol.*, 5:1694, 1985). The prevalent finding of hypermethylated 5' GSTP1 regulatory sequences in human prostatic cancers, but not normal tissues, supports this general proposal. Unfortunately, the mechanism by which de novo regional hypermethylation of specific autosomal alleles occurs in cancer cells has not been well established. Abnormal DNA methylation accompanying neoplastic cells. Both increased DNA methyltransferase activity (T. L. Kautainien, et al., *J. Biol. Chem.*, 261:1594, 1986), and elevated DNA-MT mRNA levels (W. S. ElDeiry, et al., *Proc. Natl. Acad. Sci. USA*, 88:3470, 1991), have been detected in neoplastic cells. Of interest, DNA-MT mRNA increases were observed early in the process of colonic carcinogenesis, even in some histologically normal colonic mucosa specimens.

The foregoing is meant to illustrate, but not to limit, the scope of the invention. Indeed, those of ordinary skill in the art can readily envision and produce further embodiments, based on the teachings herein, without undue experimentation.

We claim:

1. A method for detecting a prostatic cell proliferative disorder associated with glutathione-S-transferase (GSTP1) in a subject comprising:

contacting a target nucleic acid in a sample of prostate tissue or biological fluid from the subject with a reagent which detects GSTP1, wherein the reagent detects methylation of the promoter region of GSTP1 when the target nucleic acid is DNA, and wherein the reagent detects the level of GSTP1 RNA when the target nucleic acid is RNA; and detecting GSTP1 target nucleic acid, wherein hypermethylation of the promoter of GSTP1 DNA, or decreased levels of GSTP1 RNA, as compared with the level of GSTP1 RNA in a normal cell, is indicative of a GSTP1-associated cell proliferative disorder in prostate tissue.

2. The method of claim 1, wherein the GSTP1 is a member of the GSTP1 π family.

3. The method of claim 1, wherein the biological fluid is selected from the group consisting of ejaculate, urine and blood.

4. The method of claim 1, wherein the reagent which detects methylation of the promoter region of GSTP1 is a restriction endonuclease.

5. The method of claim 4, wherein the restriction endonuclease is methylation sensitive.

6. The method of claim 5, wherein the restriction endonuclease is selected from the group consisting of MspI, HpaII and BssHII.

7. The method of claim 1, wherein the reagent is a nucleic acid probe.

8. The method of claim 7, wherein the probe is detectably labeled.

9. The method of claim 8, wherein the label is selected from the group consisting of a radioisotope, a bioluminescent compound, a chemiluminescent compound, a fluorescent compound, a metal chelate, and an enzyme.

10. The method of claim 1, wherein the cell is an epithelial cell.

* * * * *